United States Patent [19]
Schoolcraft

[11] Patent Number: 5,782,141
[45] Date of Patent: Jul. 21, 1998

[54] ENGINE HAVING A NON-INTRUSIVE SELF CLOSING VALVE FOR MAGNETIC CHIP DETECTORS

[75] Inventor: Ronald J. Schoolcraft, Martinsville, Ind.

[73] Assignee: Allison Engine Company, Indianapolis, Ind.

[21] Appl. No.: 398,751

[22] Filed: Mar. 6, 1995

[51] Int. Cl.⁶ .............................. F16H 57/02; B03C 1/30
[52] U.S. Cl. ............................... 74/606 R; 210/222
[58] Field of Search ........................ 74/606 R; 210/222, 210/223; 251/149.2, 149.3

[56] References Cited

U.S. PATENT DOCUMENTS

| | | | |
|---|---|---|---|
| 568,669 | 9/1896 | Ellsworth | 251/149.3 |
| 584,091 | 6/1897 | Leidich . | |
| 2,704,156 | 3/1955 | Botstiber | 210/222 |
| 3,283,905 | 11/1966 | Cass . | |
| 3,370,144 | 2/1968 | Arthur et al. | 210/222 |
| 3,373,352 | 3/1968 | Huigens . | |
| 3,442,248 | 5/1969 | Parkinson et al. | 210/222 X |
| 3,753,442 | 8/1973 | Tauber | 210/222 X |
| 3,869,391 | 3/1975 | Kramer . | |
| 4,823,625 | 4/1989 | Hamilton . | |
| 4,839,041 | 6/1989 | Kuwayama et al. . | |
| 5,152,372 | 10/1992 | Volman . | |

FOREIGN PATENT DOCUMENTS 1 227 494  4/1971  United Kingdom ................ 210/222

*Primary Examiner*—Charles A. Marmor
*Assistant Examiner*—Mary Ann Battista
*Attorney, Agent, or Firm*—Woodard, Emhardt, Naughton, Moriarty & McNett Patent and Trademark Attorneys

[57] ABSTRACT

A self closing valve for use with an engine that prevents the loss of fluid from a transmission connected to the engine when a magnetic chip detector is removed from the transmission housing. The self closing valve and magnetic chip detector being integrated together to form a magnetic chip detection system that provides an indicating signal to the operator of an aircraft when magnetically attractable debris is detected in the transmission. The self closing valve includes a pair of valve doors that rotate about a pivot point so as to be moveable from a central region of a passageway within the transmission housing. Further, the valve does not extend substantially into the interior of the mechanical housing but is closeable to prevent loss of fluid from the interior of the mechanical housing when the magnetic chip detector is withdrawn from the passageway.

39 Claims, 7 Drawing Sheets

ENGINE HAVING A NON-INTRUSIVE SELF CLOSING VALVE FOR MAGNETIC CHIP DETECTORS

BACKGROUND OF THE INVENTION

The present invention relates generally to the design and construction of a magnetic chip detector system for engines including their associated transmissions. One application is for improving the flight safety and air worthiness of a helicopter. More particularly, the present invention has one application wherein a self closing valve is utilized to control the leakage of lubrication from an engine transmission assembly when the magnetic chip detector is removed. Although the invention was developed for use in a transmission coupled to a gas turbine engine, certain applications may be outside of this field.

It is well known that the flight capability of a helicopter is provided largely by a main rotor that is mounted onto a main rotor shaft. The main rotor shaft is driven by power from the gas turbine engine which is delivered through the main transmission. In a helicopter, the main transmission reduces the rate of revolution of a gas turbine engine to the desired rate for rotating the main rotor.

In the transmission assembly, where metal components such as gears are continually meshing or otherwise making contact with each other, metal fragments tend to be chipped from the components. The fragments, chips and particles further abrade the metal components thus creating yet more chips and particles and so causing further deterioration of the transmission. Periodically, therefore, it may be necessary to replace worn components so as to facilitate continued efficient functioning of the transmission.

The accumulation of metal fragments, chips and particles can lead to the clogging of internal lubricant flow passages within the transmission and lead to the reduced cooling by the lubricant. In an extreme case the continued deterioration of the metal components and the associated accumulation of metal chips and particles within the transmission could lead to a complete catastrophic breakdown while the helicopter is in flight. It is therefore, known to utilize a magnetic chip detector within the main transmission of a helicopter propulsion system.

A conventional magnetic chip detector comprises a magnet and an electrode, electrically insulated from each other, and mounted within the transmission so as to be exposed to the flow of lubricant. The position of the magnetic chip detector within the transmission is designed such that any substantial particles or metal chips should be carried into the proximity of the magnetic chip-detector. The magnetic force of the magnetic chip detector draws the magnetic chips into contact with the detector. Generally, when a metallic chip contacts the magnetic chip detector it makes electrical contact with the electrodes and a complete circuit is formed. After a metallic chip has completed the circuit, the magnetic chip detector sends a warning signal to the cockpit of the helicopter to alert the flight crew of the incident. An analysis of the metallic chips captured by the magnetic chip detector will enable the service technicians to monitor the health of the transmission and to determine the likelihood of failure of the mechanical components within the transmission.

Magnetic chip detector systems are generally serviced by removing the magnetic detector from the transmission. Modern designers of magnetic chip detector systems have generally used a quick disconnect to disengage the detector from the transmission. Upon removal of the detector from the transmission in certain prior systems there remains an open pathway for the leakage of lubricant. A conventional design to minimize or eliminate the leakage of lubricant from the transmission housing has been to include a self closing plunger type valve that closes when the magnetic chip detector is removed.

With reference to FIG. 1, there is illustrated a self closing plunger type valve (a) that is generally known and utilized in the industry. The self closing plunger type valve (a) uses a spring biased plunger (b) that engages a housing (c) when the magnetic chip detector (d) has been disengaged from the transmission. Upon removal of the magnetic chip detector (d) the plunger (b) is forced into a sealing engagement with housing (c) to block the flow of lubricant from the transmission.

The prior art self closing plunger type valves have a number of limitations when utilized with a magnetic chip detector. One limitation is that the valve assembly is positioned within the oil flow passageway and can block a significant portion of the passageway. The blockage of a significant portion of the passageway by the self closing plunger type valve reduces the flow of lubricant and disrupts the fluid flow. A second limitation relating to the use of a self closing plunger type valve is that the frame (e) shrouds a portion of the magnetic chip detector, thereby preventing the force of the magnetic chip detector from attracting a portion of the metallic chips in the lubricant. This shrouding phenomenon can prevent the flight crew and service technicians from obtaining an accurate assessment of the state of the metallic components in the transmission.

Furthermore, with the self closing plunger type valve being positioned within the flow stream it is contacted by chips and particles that can prevent the sealing engagement of plunger (b) with housing (c) when the valve (a) closes. If the plunger (b) cannot seat with the housing (c) a flow of lubricant will be drained from the transmission.

Even with the variety of self closing valves for magnetic chip detects, there remains a need for an improved self closing valve for magnetic chip detectors. The present invention satisfies this need in a novel and unobvious way.

SUMMARY OF THE INVENTION

To address the unmet needs of prior self closing valves for magnetic chip detectors, the present invention contemplates a combination comprising: an engine: a gear train connecting to the engine; a mechanical housing having an interior volume, the mechanical housing having the gear train disposed therein; a magnetic chip detector for attracting and indicating the presence of magnetically attractable debris in the mechanical housing; a passageway extending through the mechanical housing, at least a portion of the magnetic chip detector passing through the passageway and being exposed to the interior of the mechanical housing; and a valve not extending substantially into the interior of the mechanical housing but being closeable to prevent the loss of fluid from the interior volume of the mechanical housing when the magnetic chip detector is withdrawn from the passageway.

One object of the present invention is to provide an improved self closing valve for magnetic chip detectors.

Related objects and advantages of the present invention will be apparent from the following description.

3

Figure 1:
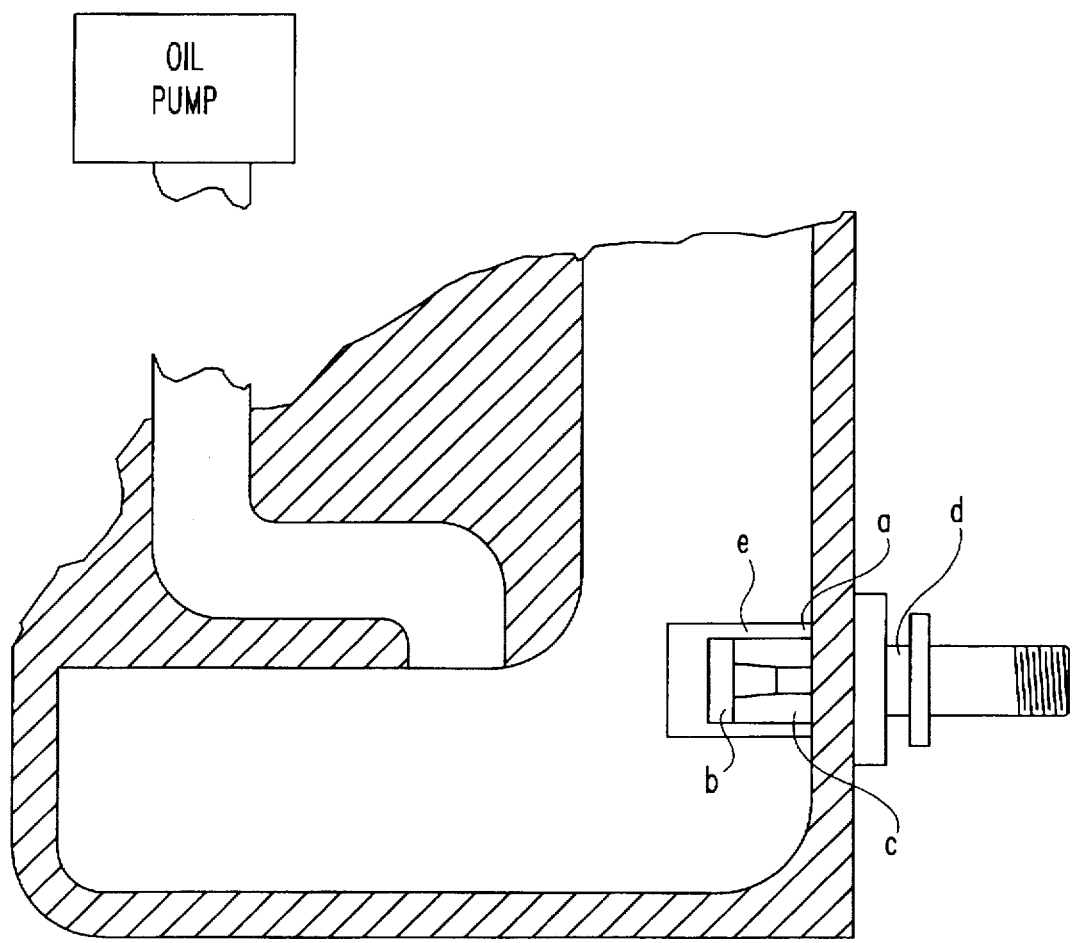
FIG. 1 is an illustrative side elevational view of a self closing plunger type valve for magnetic chip detectors positioned within an oil passageway of a transmission.
Figure 2:
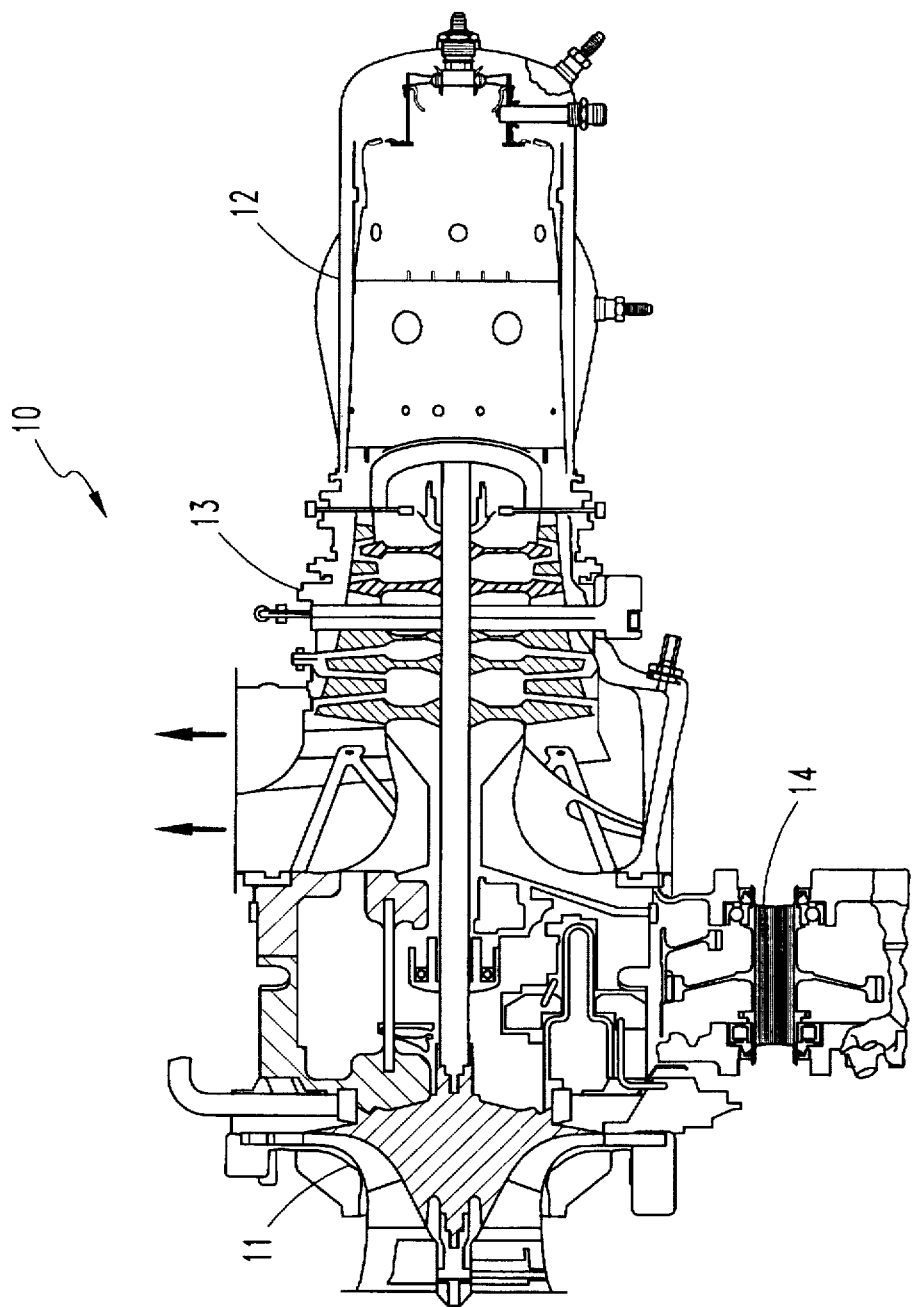

FIG. 2 is a side elevational view of a helicopter propulsion system comprising a gas turbine engine connected to a transmission.

Figure 3:
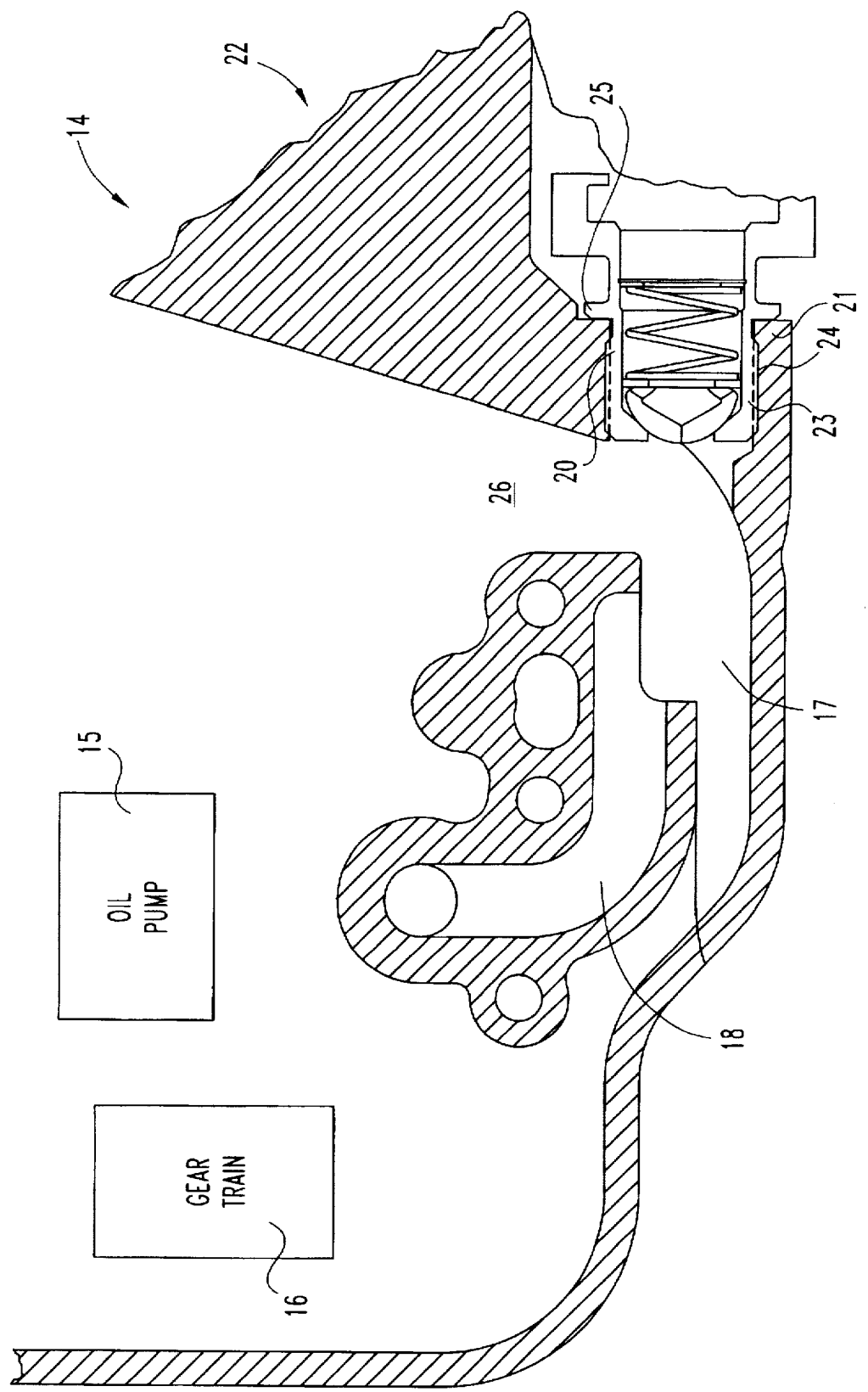

FIG. 3 is an illustrative view showing a self closing valve for magnetic chip detectors according to one form of the present invention as installed in a transmission of FIG. 2.

Figure 4:
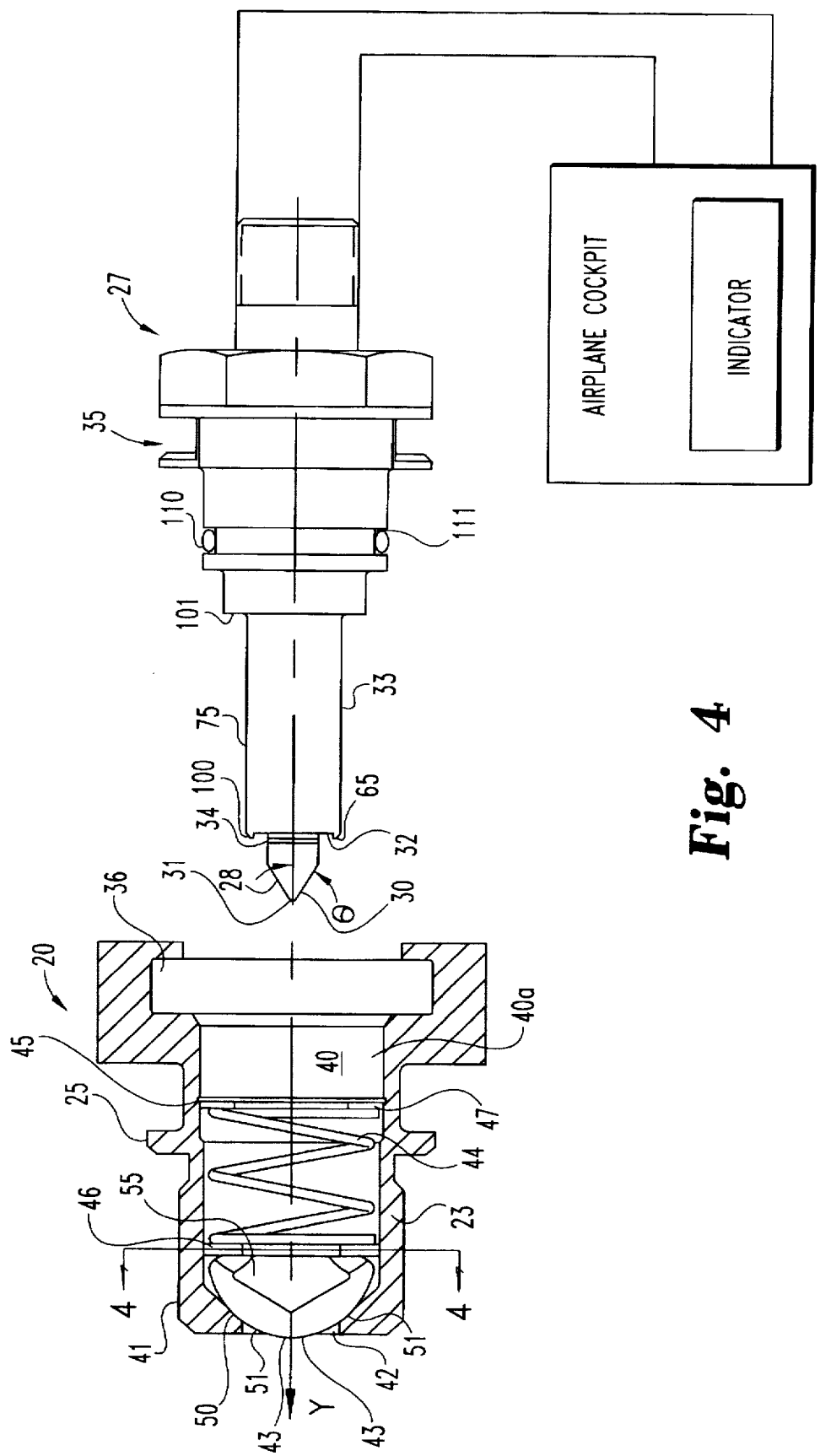

FIG. 4 is a partially exploded side elevational view of the self closing valve for magnetic chip detectors of FIG. 3.

Figure 5:
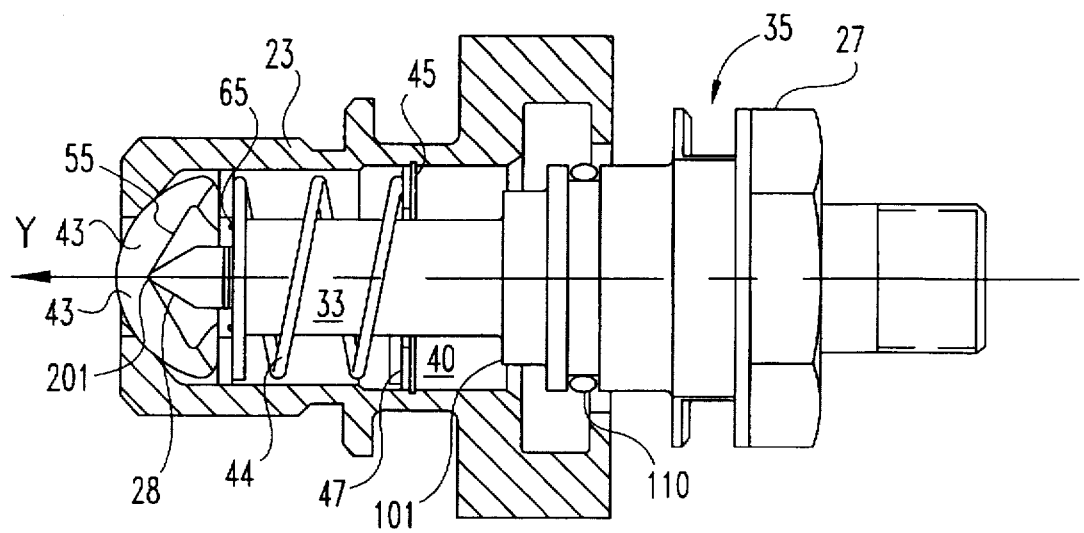

FIG. 5 is a side elevational view of the self closing valve for magnetic chip detectors of FIG. 3 in a closed position.

Figure 6:
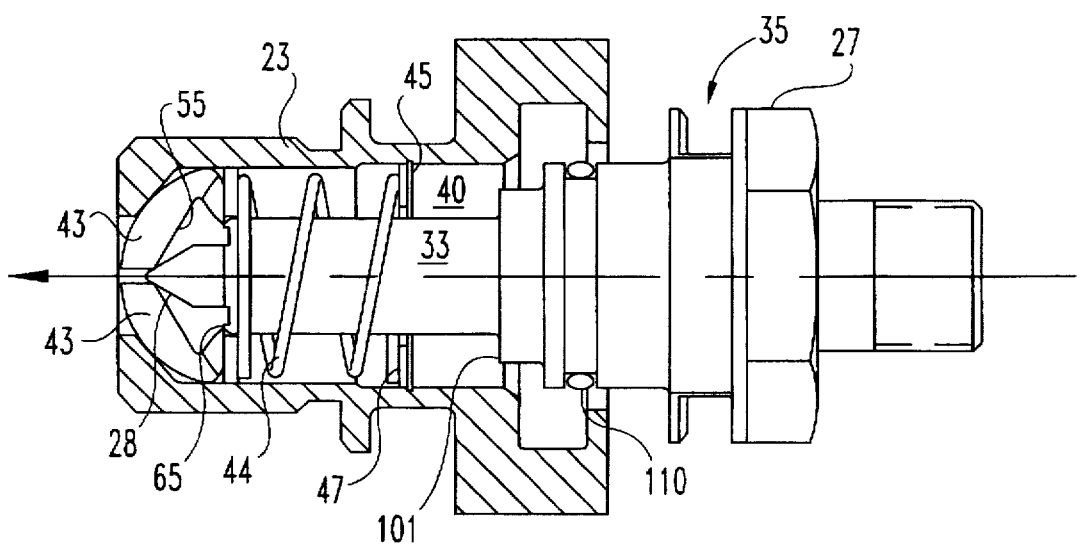

FIG. 6 is a side elevational view of the self closing valve for magnetic chip detectors of FIG. 3 with the doors comprising a portion of the self closing valve being partially opened by the magnetic chip detector.

Figure 7:
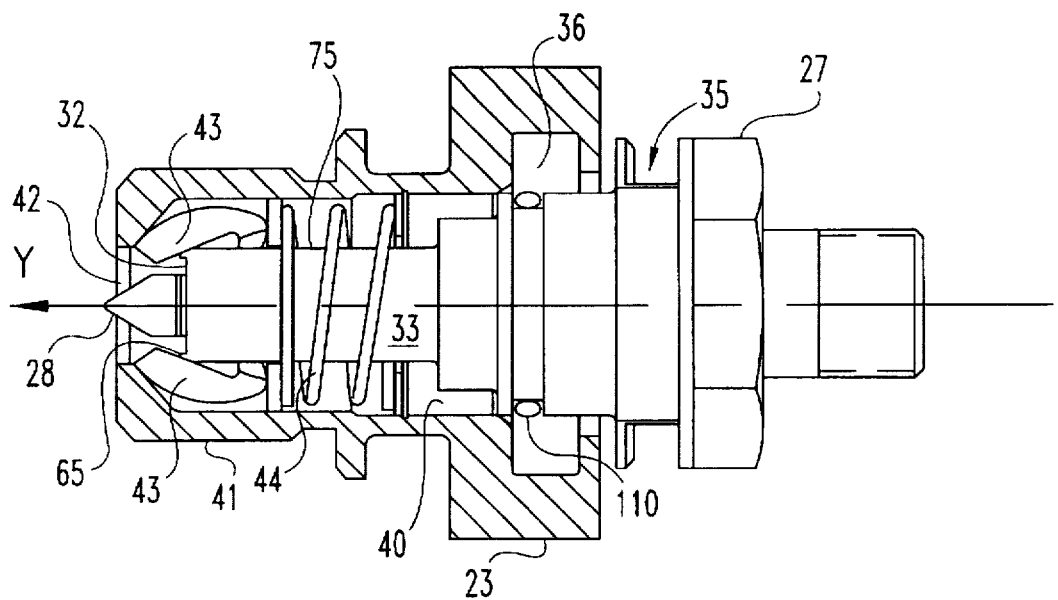

FIG. 7 is a side elevational view of the self closing valve for magnetic chip detectors of FIG. 3, with the doors comprising a portion of the self closing valve being substantially opened by the magnetic chip detector.

Figure 8:
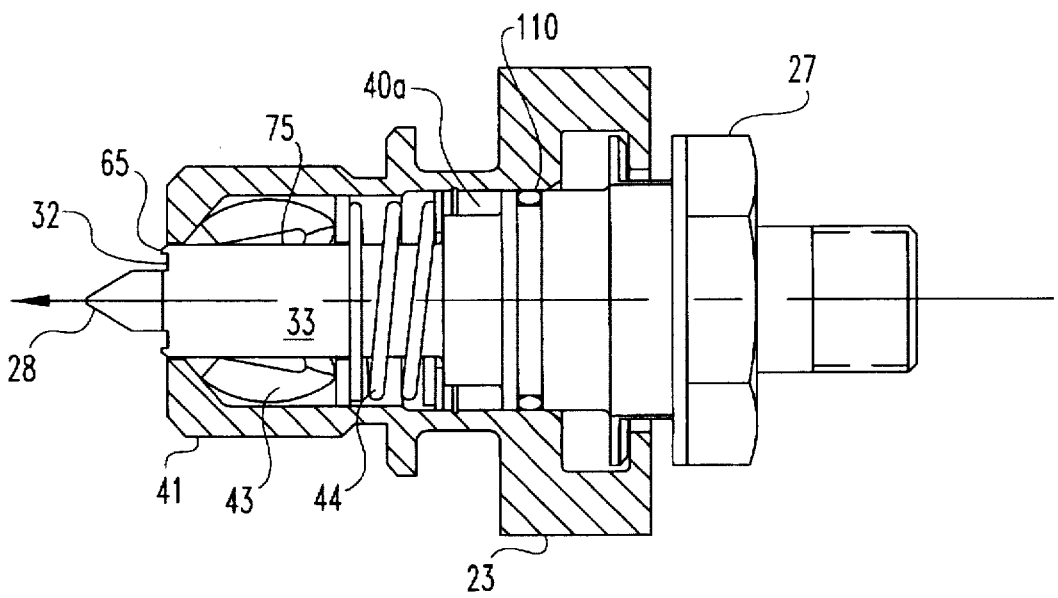

FIG. 8 is a side elevational view of the self closing valve for magnetic chip detector of FIG. 3 with the valve being open.

Figure 9:
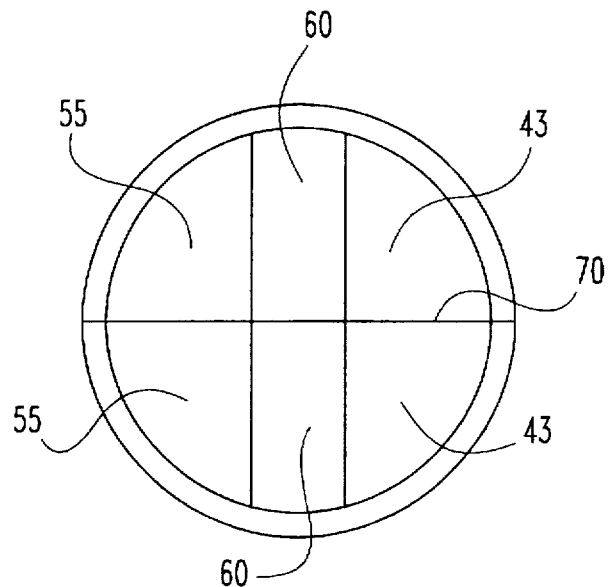

FIG. 9 is a end view taken along line 4—4 of FIG. 4 illustrating the self closing doors that comprise a portion of the self closing valve for magnetic chip detectors.

Figure 10:
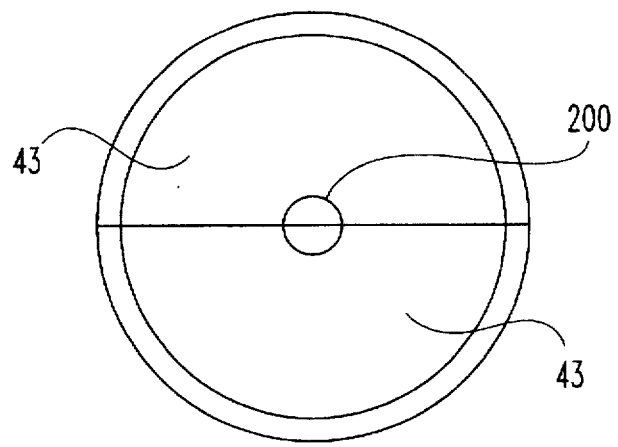

FIG. 10 is an end view taken along line 4—4 of FIG. 4 illustrating the self closing doors that comprise a portion of the self closing valve for magnetic chip detectors according to another form of the present invention.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 2, there is illustrated a gas turbine engine 10 which includes a compressor section 11, a combustor section 12, and a turbine section 13. The three main components have been integrated together with a transmission 14 to produce an aircraft flight propulsion system. One aircraft engine of this general type is a model 250, that is produced by Allison Engine Company; Inc., of Indianapolis, Ind. The aircraft flight propulsion system that is illustrated in FIG. 2, is designed for a helicopter. It is important to realize that there are a multitude of ways in which the components could be linked together. Further, a gas turbine engine connecting to a transmission is equally well suited for industrial applications. Historically, there has been widespread application of industrial gas turbine engines, such as pumping sets for gas and oil transmission lines, electricity generation, and naval propulsion.

With reference to FIG. 3, there is illustrated a fragmentary sectional view of the transmission 14. An oil pump 15 positioned within the transmission 14 for delivering a cooling fluid that is utilized to cool and lubricate the gear train 16, bearings, and other mechanical components that are positioned within the transmission 14. The mechanical contact between the rotating gears within the gear train 16 causes wear which introduces metallic chips, particles and fragments into the transmission 14. The particles normally being suspended in the lubricant and circulated through the sump 17 and internal fluid passageways 18. The sump 17 functions as a reservoir for retaining the cooling fluid.

In the preferred embodiment a self closing valve 20 for use with magnetic detectors is positioned proximate the sump 17. It is understood that the self closing valve 20 could be utilized with devices such as a magnetic collector, or other sensors that need exposure to the interior of the transmission 14. In alternate forms of the present invention the self closing valve 20 is positioned in other locations in the transmission 14. Further, the self closing valve can be utilized in transmissions coupled to other types of power plants, such as reciprocating and rotary engines. The self closing valve 20 being connected to a wall member 21 which comprises a portion of the transmission housing 22. A portion of the housing 23 being externally threaded to engage a correspondingly threaded aperture 24 formed in wall member 21. A circumferential annular stop 25 is formed around the housing 23 for limiting the distance that the valve 20 can be inserted into the transmission housing 14. In the preferred embodiment the valve 20 does not substantially extend into the interior volume 26 of the transmission 14, and therefore does not substantially block or change the flow of cooling fluid within the transmission housing 22.

With reference to FIGS. 4–8, there is illustrated the self closing valve 20 and a magnetic chip detector 27. The two components 20 and 27 interengage to create a magnetic chip detector with a self closing valve. The magnetic chip detector 27 includes a tip 28 that is formed of a non-magnetic material, such as a polymer, a non-ferromagnetic material, or other materials yielding the desired non-magnetic property. Further, the tip 28 has sufficient hardness and resistance to abrasive wear so as to not to substantially deflect or readily wear. In the preferred embodiment tip 28 is formed of stainless steel.

In the preferred embodiment tip 28 is a right circular cone having an outer surface 30 formed at an acute angle θ to the centerline Y. It is preferred that the acute angle θ is about 30 degrees. It is understood that other values of θ can be utilized, however they effect the altitude of the cone and the bluntness of the distal end 31 of tip 28. A magnet 32 is positioned within the body 33 of the chip detector 27 and has an attractive force for attracting magnetically attractable debris thereto. The contact of the magnetically attractable debris with the magnet 32 and a ring 34 completes a circuit which provides the enabling signal to the indicator device within the cockpit. An insulator 100 is disposed adjacent the ring 34. It is understood that the connecting ring 34 and the magnet 32 can have a gap therebetween that is either axial or radial. The magnetically attractable debris generally found in the transmission housing 22 are chips, fragments, and particles from the gear train 16, retaining rings, bearings, and other metallic components within the transmission 14.

The magnetic chip detector 27 includes a bayonet quick disconnect 35 that interengages with the mating receptacle 36 formed in the valve 20. The magnetic chip detector 27 being connected through a wiring harness (not illustrated) to the indicator in the cockpit.

The valve 20 includes a substantially cylindrical housing 23 having the annular stop 25 and the bayonet quick disconnect receptacle 36 extending radially therefrom. A substantially cylindrical passageway 40 is formed axially (substantially parallel with centerline y) in the housing 23. The insertion end 41 of the housing 23 being externally threaded, and having an aperture 42 therethrough. The passageway 40 and aperture 42 form an axial passageway that allows the passage of the magnetic chip detector 27 through the valve 20.

A pair of rotatable valve doors 43 are positioned within the passageway 40 of the valve housing 23. The valve doors 43 being formed of a non-magnetic material, such as a polymer, a non-ferromagnetic material, or other material yielding the desired non-magnetic property. The valve doors 43 being normally spring biased closed by a spring force exerted by spring 44. The spring 44 is disposed between a retaining ring 45 and the pair of valve doors 43. In the preferred embodiment a flat washer 46 is positioned between the valve doors 43 and the spring 44. An analogous flat washer 47 is disposed between the retaining ring 45 and the spring 44. When the valve doors 43 are spring biased closed a substantially fluid tight seal seal is created between the surface 50 of the housing 23 and a surface 51 on the valve doors 43. In another form of the present invention a coating is applied to the surface 50 and/or the surface 51 to improve the sealing characteristic of the mating parts.

In the preferred embodiment the surface 50 formed within the housing 23 is conical. In another form of the present invention the surface 50 is spherical. With reference to FIG. 9, there is illustrated an end view of the preferred embodiment of valve doors 43 taken along line 4—4 of FIG. 4. In the preferred embodiment a surface 55 is defined on the valve doors 43 and forms a right circular cone when the pair of doors 43 are aligned. A pair of reliefs 60 are formed on the surface 55 and in the preferred embodiment the pair of reliefs 60 have a semi-circle cross section. The pair of reliefs 60 provide clearance between the valve doors 43 and the body 33 of the magnetic chip detector 27. With reference to FIG. 10, there is illustrated an alternate form of the present invention wherein a conical relief 200 is formed centrally in the pair of adjoining door 43. The conical relief is engaged at it's apex by the tip 28 of the magnetic chip detector 27 in order to open the valve doors 43.

The body 33 of the magnetic chip detector 27 passes through the flat washers 46 and 47, the spring 44 and engages the pair of doors 43 at the apex of the cone formed on surface 55. The tip 28 engages the apex 201 of the cone of surface 55 and during installation of the magnetic chip detector 27 functions to transmit the force necessary to open the doors 43. As the magnetic chip detector 27 is advanced substantially axially within the housing 23 the tip 28 is utilized to push the valve doors 43 apart. The force exerted in installing the magnetic chip detector 27 is sufficient to overcome the resistance of the spring 44. Valve doors 43 function as the mechanical link to transfer the force, exerted by the pushing of the magnetic chip detector 27 into the housing 23, to compress spring 44 against the retaining ring 45 as the valve doors 43 rotate out of the central region of the passageway 40. As the valve doors 43 rotate about their pivot point, the region of mechanical contact transitions from the tip 28 of magnetic chip detector 27 to an annular ring 65 formed on the body 33. The transition of contact from the tip 28 to the annular ring 65 is designed to avoid dislodging any magnetically attractable debris contacting magnet 32. The valve doors 43 continue to open as the magnetic chip detector 27 is advanced through the passageway within the housing 23, and the valve doors 43 slide along the outside surface 75 of the body 33 to a fully open position.

The magnetic chip detector 27 has now been advanced sufficiently within the housing 23 to completely open the doors 43. The magnetic chip detector 27 is now exposed to and located proximate the interior volume 26 of the transmission 14 to facilitate attracting and capturing magnetically attractable debris thereto.

In order to complete the installation of the magnetic chip detector 27 to the transmission 14 it is necessary to engage the bayonet quick disconnect 35. The coupling of the bayonet quick disconnect 35 to the receptacle 36 requires pushing a shoulder 101 of the magnetic chip detector 27 into contact with the washer 47 and rotating the magnetic chip detector 27. As an external force is applied to the chip detector 27, the shoulder 101 and washer 47 move axially to compresses spring 44; spring 44 provides the necessary force to keep the bayonet quick disconnect 35 feature engaged. An o-ring 110 is positioned within an annular groove 111 on the body 33 of the magnetic chip detector 27. The o-ring 110 provides a fluid tight seal with the substantially cylindrical surface 40a of passageway 40 when the bayonet quick disconnect 35 has been engaged. The o-ring seal provides a substantially fluid tight seal to block the leakage of fluid from the transmission 14.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. In combination:

an engine;

a gear train coupled to said engine;

a mechanical housing having an interior with a quantity of fluid therein, said mechanical housing having said sear train disposed therein;

a magnetic chip-detector for attracting and indicating the presence of magnetically attractable debris in said mechanical housing;

a passageway extending through said mechanical housing, at least a portion of said magnetic chip detector passing through said passsageway and being exposed to said interior of said mechanical housing; and a valve positioned so as not to extend substantially into said interior of said mechanical housing but being closeable to prevent the loss of fluid from said interior of said mechanical housing when said magnetic chip detector is withdrawn from said passageway, said valve having a rotatable closure member including a plurality of valve doors positioned within said valve that are moveable along a surface of said valve to a substantially closed position.

2. The combination of claim 1, wherein said magnetic chip detector has a tip and an annular ring, and wherein during axial advancement of the magnetic chip detector relative to said valve, contact between said magnetic chip detector and said valve transitions from said tip to said annular ring.

3. The combination of claim 1, wherein said valve further includes a stop for limiting the insertion of said valve into said mechanical housing.

4. The combination of claim 1, wherein said engine defines a yes turbine engine.

5. The combination of claim 2, wherein said plurality of valve doors are rotatable.

6. The combination of claim 5, wherein said plurality of valve doors defines a pair of valve doors.

7. The combination of claim 1, wherein said pair of valve doors are normally spring biased closed.

8. The combination claim 7, wherein said pair of valve doors are self-closing when said magnetic chip detector is removed.

9. The combination of claim 7, wherein said valve further includes a salve housing, said valve housing having a sealing surface which is engageable by said pair of valve doors.

10. The combination of claim 9, wherein the engagement of said pair of valve doors with said sealing surface effects a substantially fluid tight seal.

11. The combination of claim 10, wherein at least a portion of said pair of valve doors has a coating thereon; and said pair of valve doors are substantially rigid.

12. The combination of claim 10, wherein said sealing surface is conical.

13. The combination of claim 12, wherein at least a portion of said pair of valve doors engageable with said sealing surface being conical.

14. The combination of claim 13, wherein said pair of valve doors are formed of a non-magnetically attractable material.

15. The combination of claim 14, wherein axial advancement of said magnetic chip detector pushes said pair of valve doors apart.

16. The combination of claim 15, wherein said pair of valve doors has an engagement surface engagable with said magnetic chip detector, said engagement surface forming a right circular cone when said pair of valve doors are positioned adjacent each other.

17. The combination of claim 16, wherein said magnetic chip detector has a tip, an annular advancement of said magnetic chip detector relative to said valve said contact surface between said magnetic chip detector and said pair of valve doors transitions from said tip to said annular ring.

18. The combination of claim 6, wherein said engagement surface on each of said pair of valve doors has a relief formed thereon.

19. The combination of claim 18, wherein said engine defines a gas turbine engine.

20. The combination of claim 18, wherein said reliefs provide clearance between said pair of valve doors and a portion of said magnetic ship detector.

21. The combination of claim 20, wherein each of said reliefs has a semi-circular cross section.

22. The combination of claim 21, wherein said valve further includes a stop for limiting the insertion of said valve into said mechanical housing.

23. The combination of claim 22, wherein said stop is a circumferential annular protuberance defined on said valve.

24. The combination of claim 23, wherein said magnetic chip detector is moveable between a first position wherein said magnetic chip detector extends into said interior of said mechanical housing, and a second position wherein said magnetic chip detector is removed from said interior of said mechanical housing, and wherein said magnetic chip detector is non-shrouded.

25. The combination of claim 24, wherein said magnetic chip detector further includes an O-ring, said O-ring engageable with a wall of said passageway when said magnetic chip detector is in said first position.

26. The combination of claim 25, wherein at least a portion of said pail of valve doors has a coating thereon.

27. The combination of claim 25, which further includes an indicator device within an aircraft, said indicator device connected to said magnetic chip detector for indicating the presence of magnetically attractable debris on said magnetic chip detector.

28. The combination of claim 25, which further includes a bayonet quick disconnect, said bayonet quick disconnect engageable with said valve.

29. In combination:

an engine;

a gear train coupled to said engine;

a mechanical housing having an interior, said mechanical housing having said gear train disposed therein;

passageway extending through said mechanical housing for allowing access to said interior of said mechanical housing; and a valve positioned relative to said passageway so as not to extend substantially into said interior of said mechanical housing and being closable to prevent the loss of fluid from said interior of said mechanical housing, said valve comprising:

a body having an aperture therethrough aligned with said passageway, said valve body having a sealing surface therein adjacent said aperture;

a plurality of interengaging doors positioned within said aperture for controlling the flow of fluid therethrough, said plurality of doors having an outer surface that is normally spring biased against said sealing surface to form a substantially fluid tight seal, wherein said plurality of doors are moveable along a surface of said body.

30. The combination of claim 29, wherein said plurality of doors are rotatable and substantially rigid.

31. The combination of claim 30, wherein said plurality of doors defines a pair of doors.

32. The combination of claim 31, wherein said sealing surface is conical.

33. The combination of claim 32, wherein a portion of said pair of doors corresponds to said sealing surface.

34. The combination of claim 33, wherein a portion of said pair of doors has a coating thereon.

35. The combination of claim 34, wherein said body is substantially cylindrical said cylindrical body having an externally threaded end for engaging said mechanical housing.

36. The combination of claim 35, which further includes a retaining ring within said aperture and a spring disposed between said retaining ring and said pair of doors.

37. The combination of claim 36, which further includes an indicator.

38. The combination of claim 37, wherein said indicator is a magnetic chip detector for indicating the presence of magnetically attractable debris in said mechanical housing.

39. The combination of claim 38, wherein a portion of said magnetic chip detector extends into said interior, said portion of said magnetic chip detector extending into said interior not being shrouded so as to not interfere with the attraction of any magnetically attractable debris.

* * * * *

UNITED STATES PATENT AND TRADEMARK OFFICE
CERTIFICATE OF CORRECTION

PATENT NO : 5,782,141
DATED : July 21, 1998
INVENTOR(S): Ronald J. Schoolcraft

It is certified that error appears in the above-identified patent and that said Letters Patent is hereby corrected as shown below:

In column. 3, line 50, please change ";" to --,--.

In column 6, line 34, please change "sear" to --gear--.

In column 6, line 63, please change "yes" to --gas--.

In column 7, line 1, please change "1" to --6--.

In column 7, line 2, please change "dosed" to --closed--.

In column 7, line 7, please change "salve" to --valve--.

In column 7, line 32, after "annular", please insert: --ring, and a contact surface, and wherein during the axial--.

In column 7, line 36, please change "6" to --17--.

In column 7, line 43, please change "ship" to --chip--.

In column 7, line 63, please change "pail" to --pair--.

UNITED STATES PATENT AND TRADEMARK OFFICE
CERTIFICATE OF CORRECTION

PATENT NO. : 5,782,141
DATED : July 21, 1998
INVENTOR(S) : Ronald J. Schoolcraft It is certified that error appears in the above-identified patent and that said Letters Patent is hereby corrected as shown below:

In column 8, line 46, please insert a comma between "cylindrical" and "said".

Signed and Sealed this

First Day of December, 1998

Attest:

BRUCE LEHMAN

Attesting Officer

Commissioner of Patents and Trademarks